United States Patent [19]

Libeskind

[11] Patent Number: 4,699,876
[45] Date of Patent: Oct. 13, 1987

[54] NONRADIOMETRIC POLYNUCLEOTIDE PROBES

[75] Inventor: Irwin C. Libeskind, Brighton, Mass.

[73] Assignee: E. I. Du Pont de Nemours and Company, Wilmington, Del.

[21] Appl. No.: 574,630

[22] Filed: Jan. 27, 1984

[51] Int. Cl.[4] .................. C12Q 1/68; C12Q 1/70; C12Q 1/56; C12N 9/96

[52] U.S. Cl. .................................. 435/5; 435/6; 435/13; 435/24; 435/34; 435/188; 935/78; 536/27; 436/811

[58] Field of Search ............... 435/7, 6, 13, 24, 5; 935/78; 436/501; 536/27

[56] References Cited

U.S. PATENT DOCUMENTS 3,654,090  4/1972  Schuurs et al. ................. 435/7
4,463,090  7/1984  Harris ............................ 435/7

OTHER PUBLICATIONS

Langer et al. Proc Natl. Acad. Sci USA 78: 6633–6637 (1981).
Stavrianopoulos et al. Chem Abst. 102: 42494u, 198.
Levin. Science 221: 1167 (1983).
Hakim (1970) Enzymol: Acta Biocatal. 38: 57–81.
Hofstee (1963) J. of Biolog. Chem. 238(10): 3235–3240.
Hofstee (1962) Biochem. Biophys. Acta. 55: 440–454.
Bobb (1966) Biochem Biophys Acta 119: 639–641.

*Primary Examiner*—Esther M. Kepplinger
*Assistant Examiner*—Jeremy Jay

[57] ABSTRACT

Nonradiometric polynucleotide probe compositions comprising zymogen-activating polypeptide reporter moieties are disclosed, in addition to detection methods and systems employing said probes.

44 Claims, No Drawings

NONRADIOMETRIC POLYNUCLEOTIDE PROBES

TECHNICAL FIELD

This invention relates to nucleic acid hybridization probes useful as research and diagnostic reagents.

BACKGROUND OF THE INVENTION

The use of DNA/RNA hybridization probes as basic research tools of molecular biology has flourished since publication of the seminal papers of Grunstein et al., *Proc. Nat. Acad. Sci. USA* 72:3961 (1975) and Southern, *J. Mol. Biol.* 98:503 (1975), which describe hybridization techniques employing radiolabeled polynucleotide probes.

The potential of polynucleotide probes as tools of clinical diagnosis is now apparent. To date, however, the outstanding majority of workers have employed probes comprising radioisotopically labeled atoms, which permit autoradiographic detection of probe/analyte hybrids with a reasonable degree of sensitivity. The applications of polynucleotide probes in clinical diagnosis have been highlighted by Lewin, *Science,* 221:1167 (1983), and Klausner et al., *Bio/Technology,* 1:471 (1983).

Conventional radiolabeled probes offer acceptable detectability thresholds, but can require lengthy periods for autoradiographic detection, and can introduce additional expenses associated with personnel monitoring and disposal of radioactive materials. Thus, nonradiometric polynucleotide probes with high sensitivity are of acute interest to the clinical and research communities as convenient, inexpensive and safe alternatives of isotopically-labeled probes.

Ward et al., published European Patent Application No. 82301804.9, publication No. 0663879, disclose probe compositions comprising purine, 7-deazapurine, or pyrimidine bases covalently coupled to a moiety capable of forming a detectable complex with a polypeptide. This moiety is coupled to purine bases at the 8-position, to deazapurine bases at the 7-position, and to pyrimidine bases at the 5-position. The resulting modified nucleotides are incorporated into DNA by nick-translation techniques.

Heller et al., published European Patent Application No. 82303701.5, publication No. 0070687, disclose a hybridization method for identification of target polynucleotides which employs light-labeled, single stranded polynucleotide reagents. Hybridization is detected by light emission, the intensity of which is related to the concentration of target polynucleotides in a sample mixture. The use of chemiluminescent, fluorescent, and phosphorescent reporter systems is disclosed. Heller et al., published European Patent Application No. 82303699.1, publication No. 0070685, disclose a homogeneous light-emitting hybridization assay employing luminescent-labeled first and second single-stranded reagent segments, which are hybridized in close proximity to one another along a target polynucleotide, such that nonradioactive energy transfer occurs between the light-emitting labels of the first segment and the fluorescent second segment. At least one of the light labels is of an absorber/emitter type, such that energy absorbed from the other light label is re-emitted at a secondary wavelength. Since such secondary emissions only occur if hybridization has taken place, the intensity of emission at the secondary wavelength is related to the concentration of target polynucleotide in the sample matrix.

These approaches to the design of efficient nonradiometric polynucleotide probes illustrate alternatives now being explored for application in novel diagnostic systems. It has now been found that ultrasensitive probe compositions can be prepared in the form of conjugates of polynucleotides and enzymatic zymogen activators, which serve to initiate cascade amplification detection rections.

SUMMARY OF THE INVENTION

The present invention provides polynucleotide probe compositions having the formula $$A(Z^1 \ldots Z^n) \quad \text{or} \quad \overline{\phantom{--}A(Z^1 \ldots Z^n)\phantom{--}} \quad (I)$$

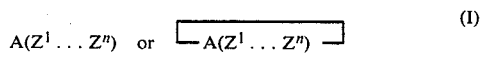

wherein
n is an integer from 2 to 500;
A is a polynucleotide having regions substantially complementary to a target polynucleotide; and
$Z^1$ through $Z^n$, which are the same or different, are nucleotide moieties which collectively form a polynucleotide sequence; provided that at least one of nucleotide moieties $Z^1$ through $Z^n$ comprises a moiety X, where X is a moiety comprising a polypeptide capable of enzymatically activating a zymogen to initiate a detectable enzymatic reaction cascade.

The invention also provides a method for detecting a target polynucleotides in a sample, comprising contacting, under hybridizing conditions, a polynucleotide probe composition as defined above, with the sample, to permit formation of probe/target hybrids; separating the probe/target hybrids from unhybridized probe composition; and contacting the probe/target hybrids with a zymogen to initiate a detectable enzymatic reaction cascade.

DETAILED DESCRIPTION OF THE INVENTION

The present invention provides nonradiometric polynucleotide probe compositions capable of forming detectable hybrids with target polynucleotides, which can be present in or derived from a variety of clinical, environmental, or biological sample matrices. The sensitivity and specificity of the probes disclosed herein renders such compositions, and methods of using said compositions, widely useful in clinical diagnosis and biological research. Examples of uses for the probes and methods of the present invention include characterization of genetic disorders, detection of particular viruses, microbes or other organisms, and identification of specific nucleic acid sequences.

The unique sensitivity and specificity of DNA hybridization probes in general, and of the probes of the present invention in particular, permit rapid and unambiguous identification not only of particular pathogens, but also of particular genetic characteristics of a pathogen, e.g., the presence in a pathogen of chromosomal or extrachromosomal elements conferring antibiotic resistance. Heretofore, identification of antibiotic resistance traits could only be accomplished through laborious and repetitive culturing steps, requiring relatively lengthy periods for completion.

As employed throughout the specification, the following definitions apply. "Polynucleotide" refers to a polymer of ribonucleic acid (RNA) or deoxyribonucleic acid (DNA), which can be single- or double-stranded, optionally incorporating synthetic, non-natural, or altered nucleotides capable of incorporation into DNA or RNA polymers. "Target polynucleotide" refers to a segment of single-stranded polynucleotide derived from a polynucleotide having a base sequence corresponding to a genetic element whose presence in a sample matrix is to be detected. "Base residue" refers to a purine, pyrimidine, modified purine, e.g., deazapurine, or modified pyrimidine moiety covalently linked by an N-glycosidic bond to a ribose or deoxyribose sugar moiety, forming a nucleotide capable of incorporation into a polynucleotide. "Zymogen" refers to any substantially inactive polypeptide precursor of an enzyme which is activated irreversibly by limited proteolysis. "Enzymatic activator," in the context of the present invention, refers to a proteolytic enzyme which reacts with zymogen to produce zymogen-derived enzyme. "Zymogen-derived enzyme" refers to a product of a reaction between zymogen and enzymatic activator, which is capable of initiating a detectable reaction or reaction cascade. "Cascade" refers to a sequence of coupled reactions in which a product of an early reaction is a catalyst for a later reaction in the sequence.

"Crosslinker" or "linking group" refers to a moiety derived from a bifunctional molecule R'—L—R", wherein R' and R" are the same or different and represent such functional groups as —NH$_2$, —CO$_2$H, —CO$_2$R, where R is 2-hydroxypyridine, N-hydroxysuccinimide, —CO$_2$Me, or other active esters, acylimidazole, maleimide, trifluoroacetate, diketone, imidoesters, sulfonate esters, imine, —CHO, 1,2-cyclohexanedione, glyoxal, sulfonyl halides, alpha halo ketones, azide, etc., and L is an alkylene or substituted alkylene group. Alkylene chain L can be substituted with such common substituents as halogen, (I, Br, Cl, F), hydroxy, cyano, phenyl, amino, carboxy, alkyl, alkoxy and others. Further, the alkylene chain of linker L can be interrupted by one or more bivalent groups, e.g., —O—, —S—, —NH—, —CH=CH—, —C≡C—, phenyl, —SO$_2$—, etc. However, functional group R' must be capable of forming, under appropriate conditions, a covalent bond with a nitrogen or carbon atom of base residue B, and functional group R" must be capable of forming, under appropriate conditions, a covalent bond with a side chain or terminal amino, carboxyl, sulfhydryl, or carbohydrate group of polypeptide enzymatic activator E, to form moiety X. Thus, bifunctional molecule R'—L—R" is reacted by appropriate techniques with a base residue or modified base residue and polypeptide E, forming a conjugate of base residue B and polypeptide E joined by an amide, ester, amine, imine, sulfonamide, thioester, phosphate, or thiophosphate linking group L, collectively forming moiety X. Clearly, the choice of linking group R'—L—R" and a particular conjugation chemistry must reflect the need to preserve other macromolecular bonds critical to the integrity of the resulting probe molecule, i.e., peptide, N-glycosidic, and phosphodiester bonds.

Alternatively, a moiety X comprising a polypeptide capable of enzymatically activating a zymogen can be coupled via a 5' phosphate or 3' hydroxyl linkage to one or more nucleotide moieties $Z^1$ through $Z^n$, or, in the alternative, directly or by an ester or other linking group to a 2', 3' or 5' carbon atom of one or more nucleotide moieites $Z^1$ through $Z^n$, forming a probe composition of the invention.

The use of an enzyme reaction cascade initiated by a zymogen-derived enzyme for detection of hybrids between target and probe polynucleotides is critical to the present invention. The outcome of such a cascade is an amplification of the number of detectable reaction events, since one molecule of a first product generated can catalyze production of numerous molecules of the second, etc. In the case of an enzyme cascade, where turnover numbers are large, significant amplification, and hence increased detection sensitivity, can be achieved.

PROBE POLYNUCLEOTIDES

As noted above, the probe compositions of the present invention can be schematically represented by the following formula

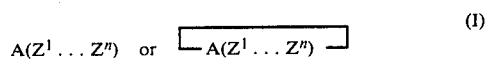

$$A(Z^1 \ldots Z^n) \quad \text{or} \quad \boxed{A(Z^1 \ldots Z^n)} \tag{I}$$

In the foregoing formulas, A represents a polynucleotide having regions substantially complementary to a target polynucleotide, and $Z^1$ through $Z^n$ are nucleotide moieties, at least one of which comprises a reporter moiety X, where X comprises a polypeptide capable of enzymatically activating a zymogen to initiate a detectable enzymatic reaction cascade. Although the probes of the invention are highly specific, complete complementarity between base sequences of probe and target polynucleotides is not necessary for hybridization, and hence, detection. In the context of the present invention, "substantially complementary" indicates sufficient homology to permit formation of stable probe-target hybrids under appropriate hybridization conditions. Polynucleotide A can comprise deoxyribonucleic acid (DNA), ribonucleic acid (RNA), certain synthetic, non-natural or altered nucleotides capable of incorporation into DNA or RNA polymers, or a combination of the foregoing nucleic acids.

Particularly useful in this invention are probes comprising a polynucleotide sequence substantially complementary to all or part of a mammalian DNA associated with a genetic disorder or to DNA of a pathogen such as a bacillus, mycobacterium, actinomycete, spirochete, rickettsia, chlamydia, mycoplasma, fungus, virus, eukaryote, multicellular organism or to a gene associated with an antibiotic resistance phenotype capable of expression by a pathogen.

Probe polynucleotide A can be conveniently isolated in useful quantities by cloning and amplification of polynucleotide sequences complementary to target polynucleotides in plasmid or phage vectors, using techniques which are now conventional to those skilled in the art. A useful reference covering most aspects of DNA manipulation is Maniatis et al., *Molecular Cloning, A Laboratory Manual,* (Cold Spring Harbor Laboratory, 1982), the disclosure of which is incorporated herein by reference.

An exemplary cloning vehicle for production of useful quantities of probe polynucleotides is plasmid pBR322 (ATCC 37017), which is described in detail by Rodriguez, et al., in Scott, ed., *Molecular Cloning of Recombinant DNA,* (Academic Press, New York, 1977), p. 73. This plasmid contains single PstI, BamI, EcoRI, HindIII, and SalI restriction endonuclease recognition sites, in addition to genes conferring resistance to the antibiotics tetracycline and ampicillin. Plasmid DNA can be amplified by growth in the presence of chloramphenicol (170 μg/ml) according to the method of Clewell, *J. Bacteriol.* 110:667 (1972); and purified by the cleared lysate procedure of Guerry et al., *J. Bacteriol.* 116:1064 (1973), prior to digestion with an appropriate endonuclease. For example, digestion with PstI inactivates the ampicillin resistance marker and generates "sticky ends" suitable for ligation to a probe polynucleotide similarly cleaved with PstI. The resulting recombinant plasmid can then be employed to transform a suitable host bacterium, e.g., *E. coli* K12 HB101. Upon growth in the presence of chloramphenicol, high plasmid copy numbers can be attained and the recombinant plasmid DNA isolated and purified as previously described.

However, a particularly preferred vector for production of probe polynucleotides is a coliphage. M13, (ATCC 15669-B1) which, like pBR322, is now commercially available (New England Nuclear Corporation, Boston, Mass., USA). DNA fragments obtained by digestion of phage DNA and DNA complementary to a target DNA of interest can be joined, amplified, and subsequently purified in single-stranded form prior to conjugation with a reporter molecule, e.g., an enzymatic activator polypeptide such as urokinase. The use of M13 phage as a cloning vehicle has been described by Messing, *Recombinant DNA Tech. Bull.* 2:43, (1979), the disclosure of which is hereby incorporated by reference.

CONJUGATION OF PROBES AND PROTEINS

Referring now to formula II, $Z^1$ through $Z^n$, which can be the same or different, are, preferably, nucleotide moieties of the formula

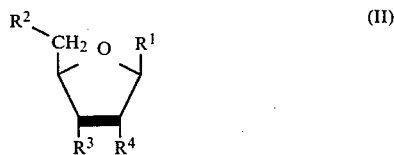

(II)

wherein
$R^1$ is $BR^5$;
where
B is a base residue; and
$R^5$ is H or X, where X is a moiety comprising a polypeptide capable of enzymatically activating a zymogen to initiate a detectable enzymatic reaction cascade;
$R^2$ and $R^3$ are H, OH, X, a phosphate group or groups, an adjacent nucleotide moiety, a phosphate group covalently linked to a moiety X or to an adjacent nucleotide moiety, or a phosphate group covalently linked to a moiety X and an adjacent nucleotide moiety; and
$R^4$ is H, OH, a phosphate group, or X; provided that, for at least one of nucleotide moieties $Z^1$ through $Z^n$, $R^1$ is $BR^5$ and $R^5$ is X; or, alternatively, $R^2$, $R^3$, or $R^4$ comprises a moiety X.

Adjacent nucleotides Z are covalently linked by formation of 3'-5' phosphodiester bonds. Superscript n, indicating the number of nucleotides, modified or unmodified, which can be added to polynucleotide A, is an integer which can vary between 2 and 500. Generally, n will have a value between 5 and 50. In general, probes comprising synthetic oligonucleotides will consist of relatively few total nucleotides, while probes derived from nucleic acid digest products will have a greater number of total nucleotides.

Base residue B can be any purine, modified purine, pyrimidine, or modified pyrimidine base capable of stable incorporation into a single-stranded polynucleotide without significantly affecting the capacity of the polynucleotide to form hybrids with target polynucleotides having substantial complementarity. However, a common feature of all base residues B useful in the present invention is a point or points suitable for covalent attachment of linking group L. Thus, apart from the "classic" bases adenine, guanine, cytosine, uracil and thymine, other, less common bases, e.g., 5-methylcytosine, 5-hydroxymethylcytosine, orotic acid derivatives, methylated bases, e.g., 1-methylguanine, etc., can optionally be incorporated into the probes of the present invention.

Further, nucleotides Z can optionally comprise various substituents, which can be linked to either base or sugar portions, and which do not deleteriously affect zymogen activation or the capability of the resulting polynucleotide to form hybrids with complementary target polynucleotides.

Polymer "tails" comprising a number of nucleotides appropriate for conjugation to a selected enzymatic activator polypeptide can be added to probe polynucleotides by use of calf-thymus terminal deoxynucleotidyl transferase (TdT), which catalyzes the addition of deoxynucleotides to the 3'-hydroxyl ends of single- or double-stranded DNA, as disclosed by Roychoudhury et al., *Nucleic Acids Res.* 3:101 (1976).

Linking group L can vary widely within the scope of the present invention. In general, L will be a linear alkylene moiety of at least three carbon atoms, optionally containing oxygen, nitrogen, or sulfur atoms, derived from a bifunctional molecule R'—L—R" capable of covalent attachment to base residue B via functional group R', and to a polynucleotide enzymatic activator E via functional group R".

Examples of bifunctional molecules suitable for conjugation of the nucleic acid/polypeptide probes of the invention include N-succinimidyl 4-glyoxalylbenzoate, carbonyl imidazole, dimethyl superimidate, 1-ethyl,3-dimethylaminopropylcarbodiimide (EDAC), para-nitrophenyl 3-(2-bromo, 3-ketobutylsulfonyl)-propionate or other active esters, glutaraldehyde, and other suitable equivalents.

Examples of preferred B-L-E conjugation techniques include the following reactions. In the formulas which follow, D refers to a ribose or deoxyribose sugar forming the remainder of nucleotide Z.

1. BISULFITE ION-CATALYZED CONJUGATION OF CYTIDYLATE NUCLEOTIDES AND ALKYL OR ARYL AMINES

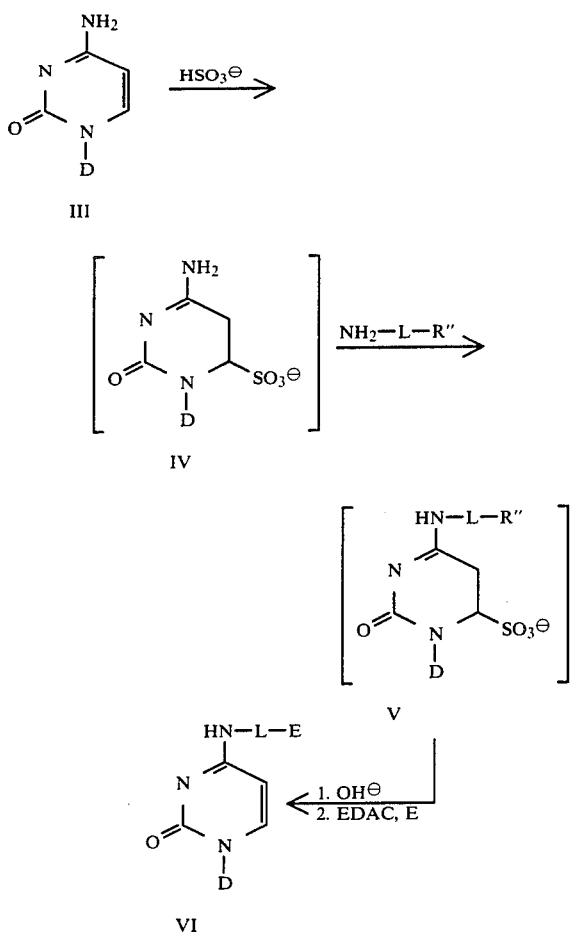

Cytidylate nucleotide residues, added to probe polynucleotides using TdT as previously described, can be converted to $N^4$-substituted cytidylate derivatives by bisulfite-catalyzed transamination with n-alkyl or alkarylamines, which serve as spacer arms linking the modified bases with enzymatic activator polypeptides X. Related conjugation chemistries have been described in detail by Shapiro et al., *Biochem. Biophys. Res. Comm.* 40:839 (1970); Boni et al., *J. Biochem.* 73:821 (1973); and Shapiro et al., "Crosslinking of Nucleic Acids and Proteins by Bisulfite", in *Advances in Experimental Medicine and Biology, Vol. A.,* (Plenum, New York, 1977) p. 634.

Referring now to the sequence of reactions above, cytidylate derivative III is reacted with bisulfite ion at a temperature of from 20°-37° C., pH 6.0-7.5, for about 6-30 hours to provide intermediate IV. Bisulfite concentrations of from 0.1M to 1M are suitable. Reaction of amine reagent $NH_2$—L—R'', where L is defined as above, provides $N^4$-substituted derivative V. Suitable amines $NH_2$—L—R'' include lysine, glycine, glycylglycine, methylamine, dimethylamine, pyrrolidine, aniline, β-naphthylamine, etc. The resulting $N^4$-alkylated cytidylate residues are then treated with base, followed by polypeptide enzymatic activator E, e.g., urokinase, in the presence of 1-ethyl-3-(3-dimethylaminopropyl)-carbodiimide (EDAC), at about 25° C. The resulting probe conjugate can be purified in good yield by chromatography upon suitable media.

Alternatively, semicarbazide hydrochloride or carbohydrazide can be employed as bifunctional linker molecules in place of the amines previously identified. The use of carbohydrazide in bisulfite-mediated conjugation reactions between polypeptides and nucleic acids is disclosed by Sarkar et al., *Methods in Enzymology Vol. LIX,* (Academic Press, New York, 1979), p. 155.

2. CONJUGATION OF 5-BROMODEOXYURIDINE AND SULFHYDRYL GROUPS ON PROTEINS

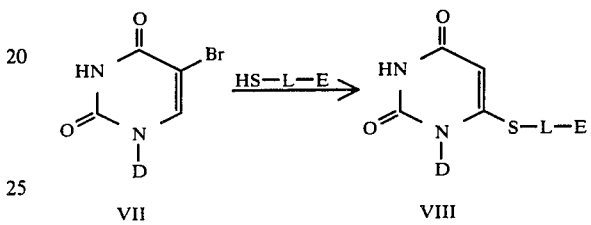

5-Bromodeoxyuridine (VII), which can be purchased from commercial sources or prepared by a method disclosed by Visser et al., *J. Am. Chem. Soc.* 75:2017 (1953), can be coupled to probe polynucleotides, for example, single-stranded M13 or pBR322 restriction fragments, using terminal deoxynucleotidyl transferase (TdT), generating a 5-bromodeoxyuridylate-tailed polynucleotide fragment.

The resulting tailed polynucleotide can then be reacted with a polypeptide enzymatic activator E, to which crosslinkers comprising pendant sulfhydryl groups have been attached. One method for attaching suitable sulfhydryl linking groups involves reaction of 2-iminothiolane.HCl with a suitable polypeptide enzymatic activator, e.g., urokinase, producing a mercaptobutyrated protein which, when reacted with a 5-bromodeoxyuridylate-tailed probe fragment, produces a conjugate of probe and protein. The probe conjugate can be separated from reagent mixtures by chromatography upon suitable media.

3. CONJUGATION OF ADENYLATE AND CYTIDYLATE NUCLEOTIDE RESIDUES WITH BROMOSULFONYL CROSSLINKERS

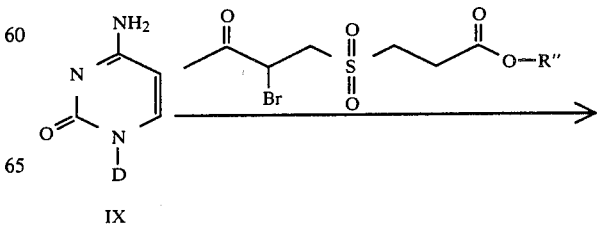

-continued

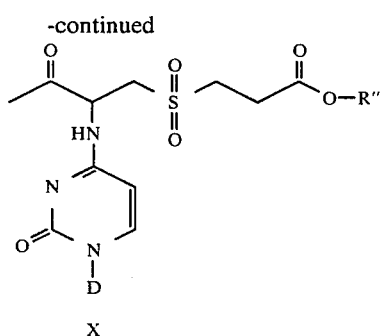

X

Certain bromosulfonyl bifunctional compounds, e.g., reactive esters of (2-bromo-3-oxobutyl sulfonyl)-propionate, react preferentially with adenylate or cytidylate nucleotides at pH values up to about 6. The resulting modified polynucleotide can then be reacted with a polypeptide enzymatic activator at pH 7.5–9 in a second reaction, resulting in acylation of lysine or other basic side chains and formation of a nucleotide-polypeptide conjugate. A preferred cross-linking reagent for this reaction is 3-(2-bromo-3-oxo-butyl sulfonyl)propionic acid p-nitrophenyl ester, which can be prepared by methods disclosed by Fink et al., *Biochem. Soc. Trans* 3:1014 (1975), or Fink et al., *Anal. Biochem.* 108:394 (1980).

4. CONJUGATION OF 4-GLYOXALYLBENZOIC ACID ESTERS AND GUANYLATE NUCLEOTIDE RESIDUES

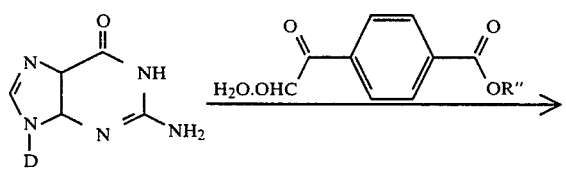

XI

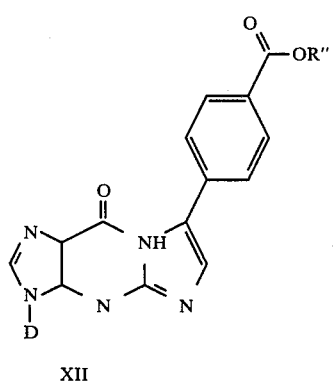

XII

Another class of bifunctional crosslinking reagents, reactive esters of 4-glyoxalylbenzoic acid, preferentially form conjugates with guanylate nucleotide residues. The resulting modified polynucleotide can then be reacted with a polypeptide enzymatic activator, e.g., urokinase, to afford a probe-polypeptide conjugate. A preferred reagent for this conjugation is succinimidyl 4-glyoxalylbenzoate.

5. CONJUGATION OF CYTIDYLATE, ADENYLATE, and GUANYLATE NUCLEOTIDE RESIDUES WITH DIMETHYLFORMAMIDE ACETALS

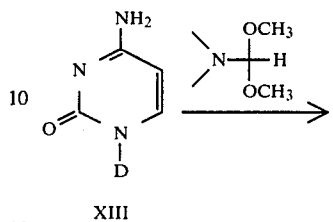

XIII

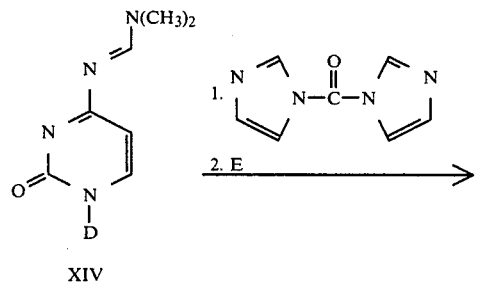

XIV

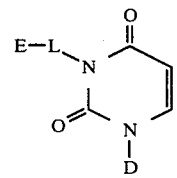

XV

Cytidylate, adenylate, and guanylate nucleotide residues can be reacted at room temperature with dimethylformamide acetals, for example, dimethylformamide diisopropyl acetal or dimethylformamide diethyl acetal, to form N-dimethylamino formamidine derivatives XIV. Holy et al., *Coll. Czech. Chem. Commun.* 39:253 (1969) disclose analogous reactions of isolated ribonucleotides. These compounds can be subsequently coupled to proteins via a nucleophilic reaction employing carbonyl diimidazole.

ZYMOGEN ACTIVATOR POLYPEPTIDES

A large number of zymogens are known which can be suitably employed in the reporter system of the probes of the present invention. Zymogen activation, as a method of detecting the presence of probe/target hybrids, offers advantages of reagent stability, increased detection sensitivity, and low background activity, or "noise".

Zymogens are convertible irreversibly by limited proteolysis to a variety of bioactive molecules. While most known zymogens are activated to enzymes, there are numerous examples in which zymogen is convertible to a peptide hormone possessing systemic activity, or to a molecule which can undergo self-assembly to produce structural cell material. A list of exemplary zymogen/zymogen-derived enzyme pairs is set forth in Table I, below:

TABLE I

| Zymogen | Bioactive Molecule |
|---|---|
| trypsinogen | trypsin |

TABLE I-continued

| Zymogen | Bioactive Molecule |
|---|---|
| chymotrypsinogen | chymotrypsin |
| procolipase | colipase |
| prophospholipase | phospholipase |
| prorennin | rennin |
| procarboxypeptidase A | carboxypeptidase A |
| procarboxypeptidase B | carboxypeptidase B |
| kininogen | kinin |
| preproelastase | elastase |
| prekallikrein | kallikrein |
| pepsinogen | pepsin |
| plasminogen | plasmin |
| fibrinogen | fibrin |
| prothrombin | thrombin |
| plasminogen proactivator | plasminogen activator |
| Cls | Cls (activated) |
| proacrosin | acrosin |
| coagulation factor XI | coagulation factor $XI_a$ |
| coagulation factor XII | coagulation factor $XII_a$ |
| coagulation factor XIII | coagulation faotor $XIII_a$ |
| procollagenase | collagenase |
| prococoonase | cocoonase |
| angiotensinogen | angiotensin |
| proinsulin | insulin |
| proparathyroid hormone | parathyroid hormone |
| proglucagon | glucagon |
| procollagen (soluble) | collagen (insoluble) |
| prochitin synthetase (yeast) | chitin synthetase |
| viral coat protein precursors (bacteriophage) | assembly-competent viral protein |
| calcium/calmodulin dependent enzymes | calcium independent enzymes |
| $NAD^+$ kinase ($Ca^{++}$ dependent) | $NAD^+$ kinase ($Ca^{++}$ independent) |
| $Ca^{++}/Mg^{++}$ ATPase, vertebrate muscle ($Ca^{++}$ dependent) | ATPase ($Ca^{++}$ independent) |
| Cyclic nucleotide phosphodiesterase ($Ca^{++}$ dependent) | Cyclic nucleotide phosphodiesterase ($Ca^{++}$ independent |

A number of biological cascades, e.g., the coagulation, complement, and digestive cascades, are known which can be utilized or adapted in the practice of the present invention. In general, a substrate reagent can be employed which reacts with zymogen-derived enzyme to produce an altered substrate morphology which can be directly observed, or alternatively, substrates can be employed which, upon reaction with zymogen-derived enzyme, produce colored, fluorescent, or phosphorescent marker materials.

Polypeptide enzymatic activator X, which converts zymogen to zymogen-derived enzyme, will usually be a protein possessing proteolytic activity. An example of a suitable activator is enteropeptidase, which converts trypsinogen to enzymatically active trypsin. A conjugate of a probe polynucleotide and enteropeptidase, following hybridization with a target polynucleotide and removal of unhybridized material, can be contacted with a detection reagent comprising trypsinogen, 5,5'-dithiobis 2-nitrobenzoic acid (DTNB, Sigma), and thiobenzyl-benzyloxycarbonyl-L-lysinate (ZLTBE, product of Peninsula Laboratories). Both enteropeptidase and trypsin-like enzymes, but not trypsinogen, rapidly cleave ZLTBE to yield, in the presence of DTNB, a colored product which absorbs at 405 nm. The amount of trypsinogen activation will be dependent upon the number of enteropeptidase-probe conjugates contacted, the resulting cascade of activated trypsin molecules cleaving substrate to form detectable product. Thus, a small number of enteropeptidase-probe conjugates present as hybrids with complementary target polynucleotides can catalyze the production of numerous trypsin molecules from trypsinogen, amplifying the number of detectable reaction events and increasing the sensitivity of the hybridization detection system.

A preferred detection system for the probes of the present invention employs conjugates of plasminogen activators, e.g., streptokinase or urokinase, and probe polynucleotides which, following hybridization and removal of unhybridized material, can be contacted with fibrin masses enriched with plasminogen. As used throughout the specification, "plasminogen activator" refers to a polypeptide capable of cleaving plasminogen to produce fibrinolytically-active plasmin. Urokinase is a potent fibrinolytic activator which, as a highly specific protease, converts the zymogen plasminogen into fibrinolytically active plasmin. Plasmin, a protease, effectively digests insoluble fibrin polymer to soluble fibrin fragments. In addition, urokinase has esterolytic and amidolytic activities.

Rapid, sensitive, and convenient assays for urokinase do exist, including fluorometric, chromogenic, caseinolytic, and fibrinolytic procedures. However, a preferred detection system utilizes the fibrinolytic properties of urokinase, where higher sensitivity results from the addition of plasminogen to synthetic fibrin clots. Thus, a proteolytic amplification cascade is generated when the resulting "enriched" fibrin plate is contacted with active urokinase. In the conventional use of such a system, a sample containing urokinase is applied to the surface of a petri dish containing fibrin polymer. After a period of time, which can vary between 1 and 18 hours at 37° C., a circular liquified area will be apparent at the point of contact, which can be easily detected with the unaided eye.

The sensitivity of the "enriched" fibrin plate assay results from the additional proteolytic amplification provided by plasminogen enrichment. Specifically, urokinase generates the fibrinolytic enzyme, plasmin, which has three functions. First, plasmin directly degrades fibrin polymer to liquid fibrin fragments. Second, plasmin acts as a weak plasminogen activator, simulating urokinase in its ability to generate additional plasmin from plasminogen. Third, plasmin converts plasminogen A to a B form, which serves to potentiate the conversion of plasminogen to plasmin by urokinase and plasmin.

Activation of plasminogen by plasminogen activators, e.g., urokinase, can be significantly potentiated by fibrin monomer, fibrinogen, fibrin(ogen) fragments, L-lysine, citrate buffers, and other agents. For example, Glu-plasminogen is activated slowly to Glu-plasmin by urokinase; the proteolytic activation cleavage by urokinase-like activators is enhanced several fold in the presence of fibrin monomer, fibrinogen, fibrin(ogen) fragments, and L-lysine. These effectors also enhance the rate of cleavage of Glu-plasminogen to Lys-plasminogen by plasmin, and once Lys-plasminogen is formed, fibrin(ogen) and fibrin(ogen) fragments bind it tightly. Lys-plasminogen is then significantly more susceptible to urokinase activation, and when bound to effector, is protected from autolysis. Overall, these mechanisms can be exploited to provide greater fibrinolysis efficiency by enhancing plasminogen activator activity as well as protecting the resulting plasmin activity from autolysis.

Other urokinase detection assays which can be adapted for use with the probes of the present invention include those disclosed by Nieuwenhuizen et al., *Anal. Biochem.* 83:143 (1977); Zimmerman et al., *Proc. Nat. Acad. Sci. USA* 75:750 (1978); Brakman et al., in *Throm-* bosis and Bleeding Disorders (Academic Press, New York 1971) p. 332; and Haverkate et al., *Thrombos. Diastes. Haemorrh. (Stuttg.)* 32:346 (1974). The former two references disclose fluorescent assays for plasmin activity, and the latter two references disclose conventional fibrin plate assay techniques.

Hybridization between the probe compositions of the invention and target polynucleotides can be accomplished by any appropriate method known to those of skill in the art. In general, a convenient and facile technique employs suitable hybridization membrane filters, to which denatured target DNA is affixed by the method of Southern, *J. Mol. Biol.* 98:503 (1975), or other suitable procedure. Optionally, 5 to 10% dextran sulfate, or other adulterants, can be incorporated into hybridization solvents to accelerate the rate of hybridization.

After hybridization with probe compositions and suitable washing steps, the resulting membrane containing immobilized probe/target hybrids can be contacted directly with an enriched fibrin plate, in the case of polynucleotide-urokinase probe conjugates, or, where appropriate, with plasminogen or suitable substrates for chromogenic or fluorescent detection.

The following Examples illustrate various aspects and embodiments of the invention. In the Examples, all parts and percentages are by weight unless otherwise indicated. All temperatures are reported in degrees Celsius, and proton nuclear magnetic resonance ($^1$H-NMR) chemical shifts are reported in $\delta$ units, parts per million downfield from internal reference tetramethylsilane.

EXAMPLES

Example 1

Conjugation of 5-Bromodeoxyuridylate Nucleotides and Urokinase 25 mg (0.18 mmol) 2-iminothiolane.HCl is added to a solution of 3 mg urokinase in 1 mL sodium borate buffer, (25 mM, pH 8.5) and allowed to incubate at 0° for 45 minutes. The resulting reaction mixture is then dialyzed against 3 changes of Tris/EDTA (tris-(hydroxymethyl)aminomethane) buffer (10 mM/0.1 mM, pH 7.4; hereinafter "TE buffer") of about 500 mL each, at about 5°. The retained portion contains mercaptobutyrated urokinase in TE buffer, free of unreacted iminothiolane and its hydrolysis products.

A mixture containing pBR322 HaeII digest (169 pmol 3' ends/mL) and 5-bromodeoxyuridine triphosphate (BUdR; 1.7 nmol/mL) in freshly prepared transferase buffer (0.1M potassium cacodylate, pH 7.2., containing 0.2 mM dithiothreitol (DTT) and 0.01M $CoCl_2$), is incubated at 15° for 15 minutes. Terminal deoxynucleotidyl transferase (TdT; 360 U/mL, 2 U/pmol 3' ends) is added and the resulting reaction mixture incubated at 15° C. for an additional 2 hours. Nucleic acid is isolated by ethanol precipitation from the reaction mixture after addition of sufficient sodium acetate (NaOAc) crystals to adjust the NaOAc concentration to 0.3M. Analysis of a [$^{32}$P]5'-end labeled portion (0.5 µg) on a DNA sequencing gel by the method of Maxam, et al., *Methods in Enzymology Vol.* 65, p. 499 (1980), indicates the approximate number of nucleotide tails added.

The BUdR tailed pBR322 fragments (100 pmol ends in TE buffer, 1 mL) are incubated with mercaptobutyrated urokinase, prepared as above (1 mL, 3 mg), at 37° for 42 hours. The resulting mixture is separated on a 1×30 cm column containing Sephadex G-100 by elution with additional TE buffer. Product pBR322-Urokinase conjugate is identified in fractions absorbing at 260 nm and fibrinolytic activity is confirmed by a standard fibrin clot assay.

Example 2

Bisulfite-catalyzed Conjugation of Deoxycytidylate-Tailed pBR322 Fragments and Urokinase Deoxycytidine-tailed pBR322 restriction fragments are prepared substantially as described in Example 1, above, for BUdR material, except that an eight-fold excess of deoxycytidine (dCTP) is employed. The resulting tailed fragments contain approximately 12–14 added dCTP residues, as determined by DNA sequencing gel analysis.

A solution of dCTP-tailed pBR322 fragments (10 $A_{260}$ U/ml) in 250 µL aqueous sodium bisulfite (0.3M, pH 7.4) containing 50 mM D-lysine is incubated at 37° for at least 20 hours. Excess bisulfite and lysine are removed by gel filtration on a 1×30 cm column containing Sephadex G-25.

Void fractions containing $A_{260}$ were treated with 0.25 mg urokinase and 50 µL 1-ethyl-3-(3-dimethylaminopropyl)carbodiimide (10 mg/mL) in TE buffer for 4 hours at 25°. The resulting conjugate is separated from other reactants on a 1×30 cm column containing Sephadex G-100 by eluting with additional TE buffer. The conjugate elutes from the column before free urokinase. Urokinase activity of the conjugate is measured by a standard fibrin clot assay.

Example 3

Bisulfite-catalyzed Conjugation of Deoxycytidylate-tailed pBR322 Fragments and Urokinase with Semicarbazide Crosslinker Substitution of 1M semicarbazide hydrochloride for D-lysine in the procedure of Example 2, above, with addition of sufficient sodium bisulfite to make 2M, affords conjugates of urokinase and dCTP-tailed pBR322 fragments.

Example 4

Conjugation of Single-stranded M13 and Urokinase with Bromosulfonyl Crosslinker

Cytomegalovirus was grown in tissue culture and viral DNA isolated from culture extracts was digested with HindIII. The HindIII twentieth fragment was cloned into pBR322 by the method of Bolivar, et al., *Methods in Enzymology* Vol. 68, (Wu, ed., Academic Press, New York, 1979). After reisolation, the resulting CMV fragment was inserted into M13 (rf form) and single-stranded phage M13-CMV DNA reisolated by the method of Messing, *Recombinant DNA Tech. Bull.* 2:43 (1979).

The resulting ssM13 phage DNA was dissolved (0.2 µg/µL) in 66 µL phosphate buffer (50 mM phosphate, 2.0M NaCl, pH 8.0) an additional 66 µL phosphate buffer added, and the resulting mixture mixed on a vortex mixer. A solution of urokinase (0.714 µg/µL) in 12 µL phosphate buffer was added with mixing, and p-nitrophenyl 3-(2-bromo-3-oxobutylsulfonyl)propionate (6 µL, 35 µg/µL) in dioxane was added at 4°. The resulting reaction mixture was allowed to stand at 4° for 66 hours. Ethanolamine (10.4 µL, 0.2 mM) in phosphate buffer was added to quench the reaction, and the mixture was allowed to stand an additional 15 minutes at 37°. The resulting mixture was then dialyzed for 18 hours against TE buffer.

The resulting conjugate was analyzed by 0.8% agarose gel electrophoresis. DNA on the gel was detected by staining with ethidium bromide, and a standard fibrin clot was poured over the gel to detect the presence of urokinase. Both a stained DNA spot and clot lysis was apparent at $R_f$ 0.57, while only lysis was present at $R_f$ 0.73, indicating unreacted urokinase.

Purification of the resulting conjugate was obtained by gel filtration on a column containing Sephadex G100, in TE buffer. The conjugate eluted in the void volume and contained urokinase activity as measured by a standard fibrin clot assay. Free urokinase eluted from the column as a second separate peak of fibrinolytic activity. The conjugate was observed to hybridize with labeled complementary material.

Example 5

Conjugation of ssM13 and Urokinase with Glyoxal Crosslinker a. Preparation of N-succinimidyl 4-glyoxalyl benzoate A mixture of selenium dioxide (2.22 g, 0.01M) in 18 mL dioxane was heated to 50° and held at this temperature until all $SeO_2$ had dissolved. To this solution was added 3.28 g 4-acetyl benzoic acid, and the resulting reaction mixture held at reflux until no additional precipitation of black, metallic selenium was observed (approximately 6 hours). Precipitate was removed by filtration through filter paper, and dioxane was evaporated under reduced pressure. A residual yellow oil was recrystallized from boiling water, affording an off-white solid, m.p. 175°–177°, $^1$H-NMR ($d_6$ DMSO): δ 5.7 (1p, br), 6.8 (2, br exchangeable), 8.2 (4p, m), of 4-glyoxalyl benzoic acid as a hydrate. Other esters can be prepared as above by adding N-hydroxysuccinimide.

222 mg (1.5 mmol) of N-hydroxysuccinimide were added to 196 mg (1 mmol) 4-glyoxalyl benzoic acid and 309 mg (1.5 mmol) dicyclohexyl carbodiimide in dry dimethylformamide. The resulting mixture was stirred under nitrogen for 16 hours at 50°, and a precipitated urea derivative which formed was removed by filtration. Ether was added dropwise to the reaction mixture and product N-succinimidyl 4-glyoxalyl benzoate precipitated as a yellow solid, $^1$H-NMR: δ 2.9 (4p, s).

b. Conjugation

Single-stranded M13 containing a cytomegaloviral insert, prepared substantially as described in Example 4, above, is equilibrated with 0.1M potassium cacodylate buffer, pH 7.5, containing 20 mM sodium borate and 10 mM $MgCl_2$. Final DNA concentration is brought to approximately 2 $A_{260}$ units/mL.

0.2 mL of a 6 mg/mL solution of succinimidyl 4-glyoxalylbenzoate in cacodylate buffer containing 3% dioxane are added to 1 mL of the foregoing ssM13 solution, and the resulting reaction mixture is incubated at 37° for 1 hour. DNA is precipitated by addition of two volumes cold ethanol at −70°, then resuspended in a solution of 200 μg/mL urokinase in sodium borate buffer (0.1M, pH 8.5) containing 0.4M NaCl. This mixture is incubated at 37° for 16 hours, and applied to a column containing Sephadex G-100 and eluted with TE buffer. The conjugate elutes in the void volume and is demonstrated to retain urokinase activity by fibrin clot assay. Free urokinase elutes as a second peak of fibrinolytic activity.

Example 6

Conjugation of Urokinase and Deoxycytidylate Tailed pBR322 with Trimethyl Orthoformate Carbonyl Imidazole Crosslinker 0.25 mL of a 100 mg/mL solution of dimethylformamide diisopropyl acetal in 50% aqueous formamide was added to 1 mL of dCTP-tailed pBR322 restriction fragments, prepared as previously described, in phosphate/EDTA buffer (0.1M 0.01M; pH 7.2) at a concentration of 2 $A_{260}$ units/mL. The resulting reaction mixture is allowed to stand at 25° for 16 hours, and extracted with 3×0.5 mL aliquots of chloroform. The DNA is precipitated with two volumes of ethanol at −70°, and is resuspended in 0.5 mL of a solution containing 0.1 mg/mL urokinase in phosphate/NaCl, pH 8.5 (0.1M/0.4M). A solution of carbonyl diimidazole (500 μL, 100 mg/mL) in dioxane is added, and this mixture incubated at 37° for 4 hours, followed by extraction with chloroform. The conjugate is separated from the reaction mixture by gel filtration on a 1×20 cm column containing Sephadex G100 in TE buffer, and elutes in the void volume, followed by a second fraction containing free urokinase, as measured by a standard fibrin clot assay.

Example 7

Detection of Cytomegalovirus in Human Urine Samples by Hybridization with Probe Conjugates a. Preparation of Fibrin Assay Plates To individual wells of a 96 well microtiter plate was added fibrin plate buffer (33 μL, 50 mM sodium barbital, 94 mM NaCl, 1.65 mM $CaCl_2$, 0.7 mM $MgCl_2$, pH 7.75, [FPB]), human fibrinogen (16 μL, obtained from Kabi Dianostica grade L, 10 mg/mL reconstituted in water), and human plasminogen (98 μL, 25 Caseinolytic Units/mL in 10 mM phosphate pH 7.75). Clotting was induced upon addition of bovine thrombin (7 μL, 10 NIH Units/mL in 0.9% Nacl). The plates are ready for use after standing at room temperature for 45 minutes.

b. Determination of Detectability Thresholds

To determine the sensitivity of the fibrin plates prepared as above, a gradient of urokinase was applied to a plate by spotting 20 μL drops, containing amounts of urokinase ranging from 0.1 fg to 1 pg, and control drops containing no urokinase, upon the polymerized fibrin surface of the plate. The microtiter plates thus prepared were incubated for 8 hours at 37°, followed by additional incubation at 25° for 16 hours. Inspection of the plates revealed no observable lysis at the locations of the control spots, or at the locations of spots containing 0.1 fg urokinase. Clear zone of lysis were apparent at all spot loci to which 1 fg or a greater amount of urokinase had been applied.

c. Hybridization and Detection

Several samples of human urine are concentrated 1000-fold by evaporation. Using a 96-grid application apparatus, the concentrated samples are applied to a hybridization membrane and allowed to dry. The membranes are not baked to effect immobilization of samples. Hybridization is effected, in a sealed plastic bag, by the method of Southern, *J. Mol. Biol.* 98:503 (1975) using a cytomegalovirus/ssM13/urokinase conjugate.

After hybridization and washing the hybridization membranes are overlayed directly, sample side down, upon a plasminogen-enriched fibrin assay plate, which is incubated at 37° for 17 hours. Zones of lysis activity are observed at locations corresponding to those at which samples of urine containing cytomegalovirus were applied.

What is claimed is:

1. A polynucleotide probe composition capable of forming hybrids with target polynucleotides which are detectable by means of an enzymatic reaction cascade of the formula

  (I)

wherein n is an integer from 2 to 500;

A is a polynucleotide having regions substantially complementary to a target polynucleotide; and $Z^1$ through $Z^n$, which are the same or different are nucleotide moieties which collectively form a polynucleotide sequence; provided that at least one of nucleotide moieties $Z^1$ through $Z^n$ comprises a moiety X, where X is a moiety comprising a proteolytic enzyme capable of enzymatically activating a zymogen to initiate a detectable enzymatic reaction cascade.

2. A composition according to claim 1, wherein A is a polynucleotide comprising a nucleotide sequence substantially complementary to all or part of a gene associated with an antibiotic resistance phenotype capable of expression by a pathogen.

3. A composition according to claim 1, wherein A is a polynucleotide comprising a nucleotide sequence substantially complementary to all or part of a mammalian DNA associated with a genetic disorder.

4. A diagnostic kit for detecting the presence of a target polynucleotide characteristic of or associated with a pathogen, a pathogen capable of expressing an antibiotic resistance phenotype, or a genetic disorder in mammals, said kit comprising a composition according to claim 1, and a detection substrate comprising a zymogen which, upon activation by a zymogen activator, is capable of initiating a detectable enzymatic reaction cascade.

5. A composition according to claim 1 wherein A is a polynucleotide comprising a nucleotide sequence substantially complementary to all or part of a structural gene characteristic of a pathogen.

6. A composition according to claim 5, wherein the pathogen is a bacillus.

7. A composition according to claim 5, wherein the pathogen is a mycobacterium, actinomycete, or spirochete.

8. A composition according to claim 5, wherein the pathogen is a rickettsia, chlamydia, or mycoplasma.

9. A composition according to claim 5, wherein the pathogen is a fungus.

10. A composition according to claim 5, wherein the pathogen is a virus.

11. A composition according to claim 5, wherein the pathogen is a eukaryote.

12. A composition according to claim 11, wherein the pathogen is a multicellular organism.

13. A method for detecting the presence of a target polynucleotide in a sample, comprising:

(a) contacting, under hybridizing conditions, a polynucleotide probe composition of claim 1 with the sample, to permit formation of probe/target hybrids;

(b) separating the probe/target hybrids from unhybridized probe composition; and (c) contacting the probe/target hybrids with a zymogen to initiate a detectable enzymatic reaction cascade.

14. A method according to claim 13, wherein the target polynucleotide is associated with an antibiotic resistance phenotype capable of expression by a pathogen.

15. A method according to claim 13, wherein the target polynucleotide represents all or part of a mammalian DNA associated with a genetic disorder.

16. A method according to claim 13, wherein the target polynucleotide is characteristic of a pathogen.

17. A method according to claim 16, wherein the pathogen is a bacillus.

18. A method according to claim 16, wherein the pathogen is a mycobacterium, actinomycete, spirochete, rickettsia, chlamydia, mycoplasma, or fungus.

19. A method according to claim 16, wherein the pathogen is virus.

20. A method according to claim 16, wherein the pathogen is a eukaryote.

21. A polynucleotide probe composition according to claim 1, said composition having the formula

  (I)

wherein n is an integer from 2 to 500;

A is a polynucleotide having regions substantially complementary to a target polynucleotide; and $Z^1$ through $Z^n$, which are the same or different, are nucleotide moieties which collectively form a polynucleotide sequence; said nucleotide moieties having the formula

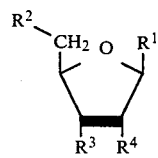  (II)

wherein $R^1$ is $BR^5$;

where

B is a base residue; and $R^5$ is H or X, where X is moiety comprising a proteolytic enzyme capable of enzymatically activating a zymogen to initiate a detectable enzymatic reaction cascade;

$R^2$ and $R^3$ are H, OH, X, a phosphate group or groups, an adjacent nucleotide moiety, a phosphate group covalently linked to a moiety X or to an adjacent nucleotide moiety, or a phosphate group covalently linked to a moiety X and an adjacent nucleotide moiety; and $R^4$ is H, OH, a phosphate group, or X; provided that, for at least one of nucleotide moieties $Z^1$ through $Z^n$, $R^1$ is $BR^5$ and $R^5$ is X; or, $R^2$, $R^3$, or $R^4$ comprises a moiety X.

22. A composition according to claim 21, wherein for at least one of nucleotide moieties $Z^1$ through $Z^n$, $R^2$ comprises a moiety X.

23. A composition according to claim 21, wherein for at least one of nucleotide moieties $Z^1$ through $Z^n$, $R^3$ comprises a moiety X.

24. A composition according to claim 21, wherein for at least one of nucleotide moieties $Z^1$ through $Z^n$, $R^4$ is X.

25. A composition according to claim 21, wherein for at least one of nucleotide moieties $Z^1$ through $Z^n$,

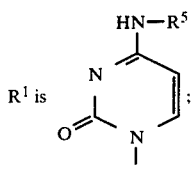

where $R^5$ is X.

26. A composition according to claim 25, wherein X is LE, where
   L is a linking group; and
   E is an enzyme having zymogen-activating activity.

27. A composition according to claim 26 wherein E is enteropeptidase.

28. A composition according to claim 26, wherein E is a plasminogen activator.

29. A composition according to claim 28, wherein E is urokinase.

30. A composition according to claim 21, wherein for at least one of nucleotide moieties $Z^1$ through $Z^n$,

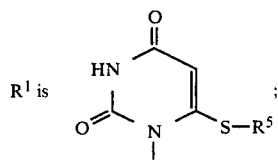

where $R^5$ is X.

31. A composition according to claim 30, wherein X is LE, where
   L is a linking group; and
   E is an enzyme having zymogen-activating activity.

32. A composition according to claim 31, wherein E is enteropeptidase.

33. A composition according to claim 31 wherein E is a plasminogen activator.

34. A composition according to claim 31 wherein E is urokinase.

35. A composition according to claim 21, wherein for at least one of nucleotide moieties $Z^1$ through $Z^n$,

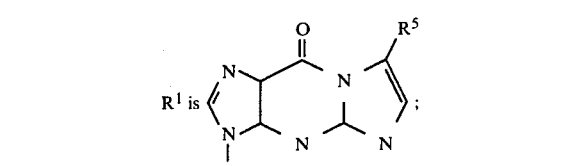

where $R^5$ is X.

36. A composition according to claim 35, wherein X is LE, where
   L is a linking group; and
   E is an enzyme having proteolytic activity.

37. A composition according to claim 36, wherein E is enteropeptidase.

38. A composition according to claim 36, wherein E is a plasminogen activator.

39. A composition according to claim 38, wherein E is urokinase.

40. A composition according to claim 21, wherein for at least one of nucleotide moieties $Z^1$ through $Z^n$,

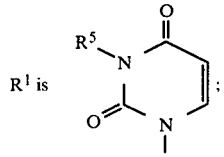

where $R^5$ is X.

41. A composition according to claim 40, wherein X is LE, where
   L is a linking group; and
   E is an enzyme having zymogen-activating activity.

42. A composition according to claim 41, wherein E is enteropeptidase.

43. A composition according to claim 41, wherein E is a plasminogen activator.

44. A composition according to claim 43, wherein E is urokinase.

* * * * *